(12) United States Patent
Scheule

(10) Patent No.: US 6,926,689 B2
(45) Date of Patent: Aug. 9, 2005

(54) AORTIC BALLOON OCCLUSION CANNULA

(76) Inventor: Albertus Scheule, Schwabstrasse 14, 72074, Tübingen (DE)

( * ) Notice: Subject to any disclaimer, the term of this patent is extended or adjusted under 35 U.S.C. 154(b) by 437 days.

(21) Appl. No.: 10/099,496

(22) Filed: Mar. 13, 2002

(65) Prior Publication Data

US 2003/0176830 A1 Sep. 18, 2003

(51) Int. Cl.[7] .......................... A61M 37/00; A61M 1/36; A61B 19/00
(52) U.S. Cl. ...................... 604/6.16; 604/4.01; 128/898; 422/45
(58) Field of Search ...................... 604/4.01, 5.01–5.04, 604/6.01, 6.06, 6.11, 6.13–6.16, 8, 19, 27, 28, 500, 507–9, 93.01, 96.01, 97.01–97.02, 98.01, 99.01, 101.01, 101.03, 101.05, 104, 523

(56) References Cited

U.S. PATENT DOCUMENTS

| | | | |
|---|---|---|---|
| 4,731,055 A | | 3/1988 | Melinyshyn et al. |
| 5,312,344 A | | 5/1994 | Grinfeld et al. |
| 5,334,142 A | | 8/1994 | Paradis |
| 5,458,574 A | * | 10/1995 | Machold et al. ....... 604/101.03 |
| 5,795,325 A | * | 8/1998 | Valley et al. ............... 604/509 |
| 6,093,166 A | * | 7/2000 | Knudson et al. ............... 604/8 |
| 6,409,751 B1 | * | 6/2002 | Hall et al. .................. 623/1.11 |
| 6,565,582 B2 | * | 5/2003 | Gifford et al. .............. 606/153 |

FOREIGN PATENT DOCUMENTS

| | | |
|---|---|---|
| DE | 19 15 933 A1 | 10/1970 |
| EP | 1086717 | 3/2001 |
| WO | WO 98/11831 | 3/1998 |

OTHER PUBLICATIONS

English Translation of International Preliminary Examination Report for corresponding PCT/DE00/03160 dated Oct. 3, 2001.

National Stage Application filed Mar. 13, 2002 entitled Aortic Balloon Occlusion Aorta by Michel Doaré with accompanying preliminary amendment dated Mar. 13, 2002.

* cited by examiner

Primary Examiner—Patricia Bianco
(74) Attorney, Agent, or Firm—Christie, Parker & Hale, LLP

(57) ABSTRACT

An aortic balloon occlusion cannula for the occlusion of the aorta ascendens during cardiac surgery including a cannula containing several lumina that are separated from one another. The cannula carriers two dilatable occlusion balloons positioned at a distance from each other, one of the balloons being neighbored to the distal end of the cannula which faces away from the heart and each of the balloons being connected to its own lumen which enables its dilation in independence from the other balloon. The cannula is insertable through the lefthand ventricle of the heart and through the valvula aortae and includes at least one further lumen. The further lumen being connected on the distal side, facing the body, of the distal occlusion balloon to the lumen of the aorta and is adapted to be connected to an extracorporal blood supply device. An additional separate lumen is provided in the cannula and forms a return conduit for liquid and opens on the proximal side of the proximal occlusion balloon.

11 Claims, 2 Drawing Sheets

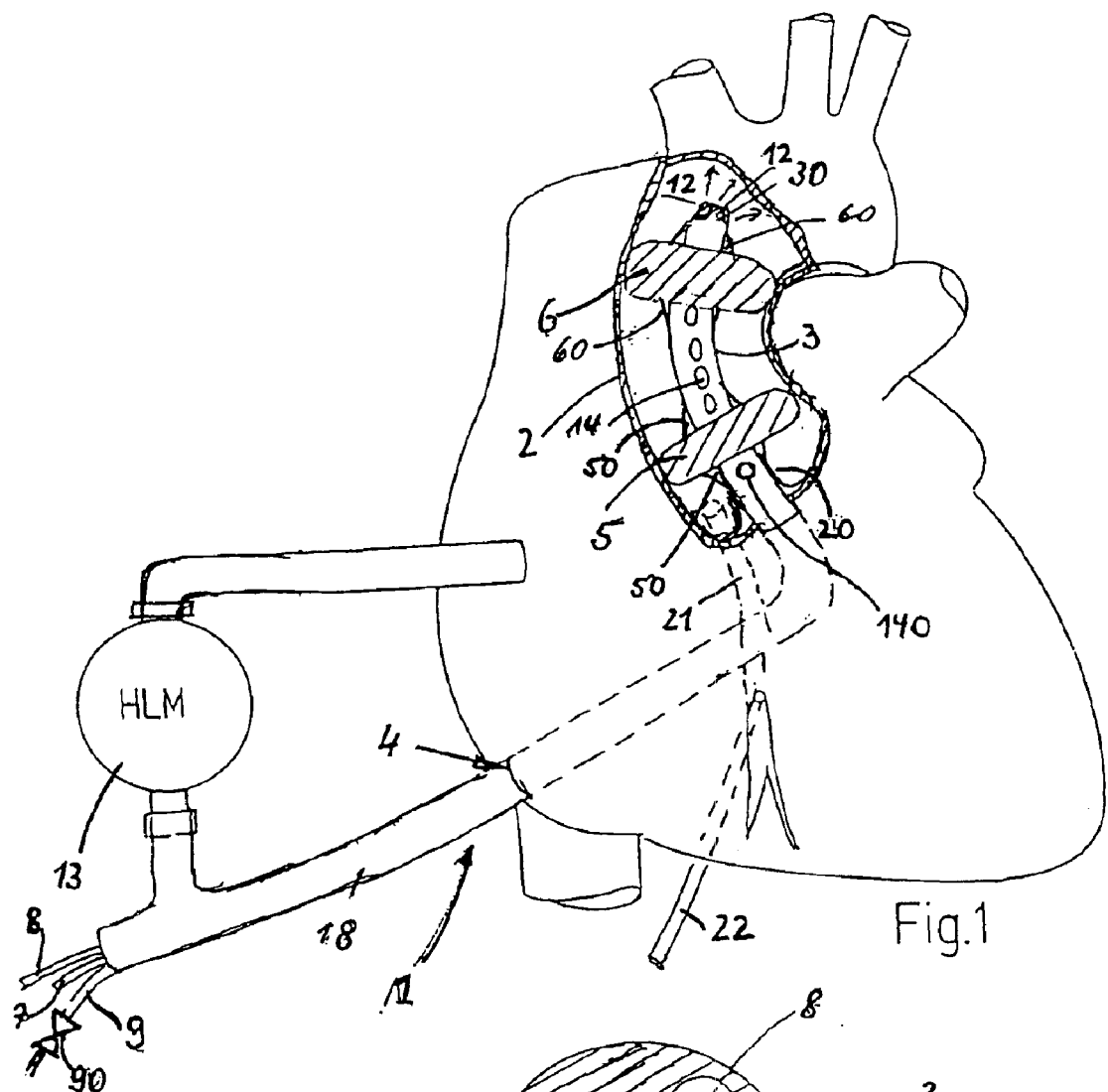
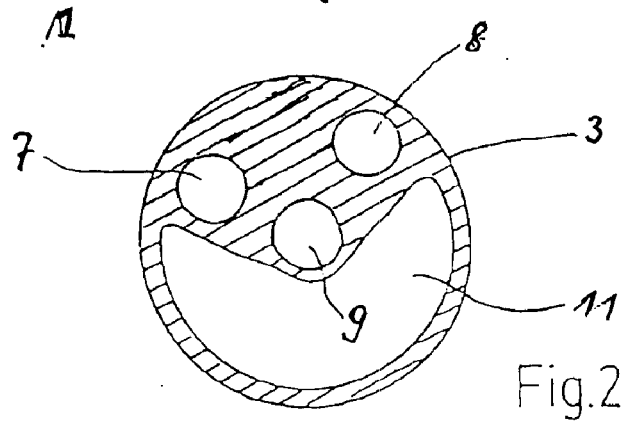

AORTIC BALLOON OCCLUSION CANNULA

BACKGROUND

The invention concerns an aortic balloon occlusion cannula for the occlusion of the ascending aorta during cardiac surgery.

An arteriosclerotically altered ascending aorta represents a problem in the field of cardiac surgery. It occurs in almost all patients who suffer from calcification of the coronary vessels or, to different degrees, in patients with valvular diseases. It is necessary to insert an aortic cannula into the ascending aorta in order to connect for instance a patient, who undergoes a bypass operation, to the extra corporal circulation (heart-lung machine). The blood circulation is separated from the heart by clamping the ascending aorta towards the heart that is proximal, with a metal clamp, which is attached at right angles. There is, however, the danger of a detachment of particles or plaques from the wall of the ascending aorta which are transported by the blood flow especially into the blood vessels of the head and therefore into the brain. This leads to embolies, which appear clinically often in form of neurological failures (cerebral infarction).

An aortic balloon occlusion cannula is known from the DE 19 15 933 A1. It is used to avoid the risks going along with aortic clamping at right angles during the extracorporeal circulation that is applied during cardiac surgeries. It includes an occlusion cannula that can be inserted into a catheter. Its lumen is connected on both sides to a dilatable balloon, which allows closing the ascending aorta from the inside by means of a balloon occlusion during the ischemic time without an aortic clamping at right angles. A similar aortic occlusion cannula has also been described in the U.S. Pat. No. 5,334,142, especially in connection with cardiopulmonary resuscitation. Further embodiments of occlusion cannulae having two dilatable balloons are disclosed in U.S. Pat. No. 5,458,574 and in EP 1 086 717 A1.

These balloon cannulae, however, do not solve the problems of other dangers, which can also lead to a calcified embolie as a result of an arteriosclerotic ascending aorta.

In order to be able to suture the vein bypass to the aorta during a bypass surgery, the aorta has to be clamped with a metal clamp over a certain length in the area of the suture. There is a considerable risk of embolie connected with this therapy. In order to provoke a cardiac arrest, it is also necessary to infuse a cardioplegic substance into the ascending aorta. It is also possible that plaques are separated if a cardioplegic conduction is inserted especially for this purpose into the ascending aorta.

BRIEF SUMMARY OF THE INVENTION

An object of this invention is to offer a solution to the above mentioned problem and to create an aortic balloon occlusion cannula for the occlusion of the ascending aorta during surgeries. This aortic balloon occlusion cannula is adapted to reduce the danger of the separation of calcified plaques from the calcified ascending aorta and to guarantee a careful treatment of the aorta during the surgery.

The new aortic cannula can be placed into the aorta via the lefthand ventricle. Thus the calcified aorta needs not to be opened and subsequently reclosed. It is just with an arteriosclerotic aorta ascendens that suturing of the aorta can be a problem which occasionally necessitates a partial clamping of this area resulting in an increased risk of embolies caused by calcified particles.

Furthermore, the new aortic cannula permits the clamping of the ascending aorta from the inside by means of a dilatable occlusion balloon. In addition, the cannula carries a second occlusion balloon that is positioned in a certain distance from the first balloon. It is able to separate an area from the perfusion. This area is determined by the distance between the two balloons. It serves then for the suture of the vein bypasses. With this, the dangerous tangential clamping of an aortic area is avoided. In the meantime, the aortic root perfusion can retrogradely be performed by means of a coronary sinus in order to reduce the ischemic time.

If the aortic root perfusion is retrogradely applied via the coronary sinus the new cannula can furthermore assume the function of sucking off the aortic root perfusion. It is one of the advantages of the new aortic cannula that, in contrast to the above discussed state of the prior art, the occlusion cannula need not be inserted through the calcified aorta and that, furthermore, the aorta need not be clamped from its outside, neither tangentially nor transversely. In addition, neither the tubing for the aortic root perfusion nor a suction tube need to be additionally inserted into the aorta through a separate further access in the aorta. Finally, the field of the surgical operation remains much clearer as it is the case with the usual technique, for the reason that there are less additional tubings and clamps that tend to encumber the operation field.

BRIEF DESCRIPTION OF THE DRAWINGS

The illustration shows an example of the subject of the invention. The following figures show:

FIG. 1 is a balloon cannula according to the invention in situ is schematic illustration;

FIG. 2 is the cannula according FIG. 1 cut lengthways along the line II—II of FIG. 1 in a schematic illustration.

DETAILED DESCRIPTION

Figure 3:
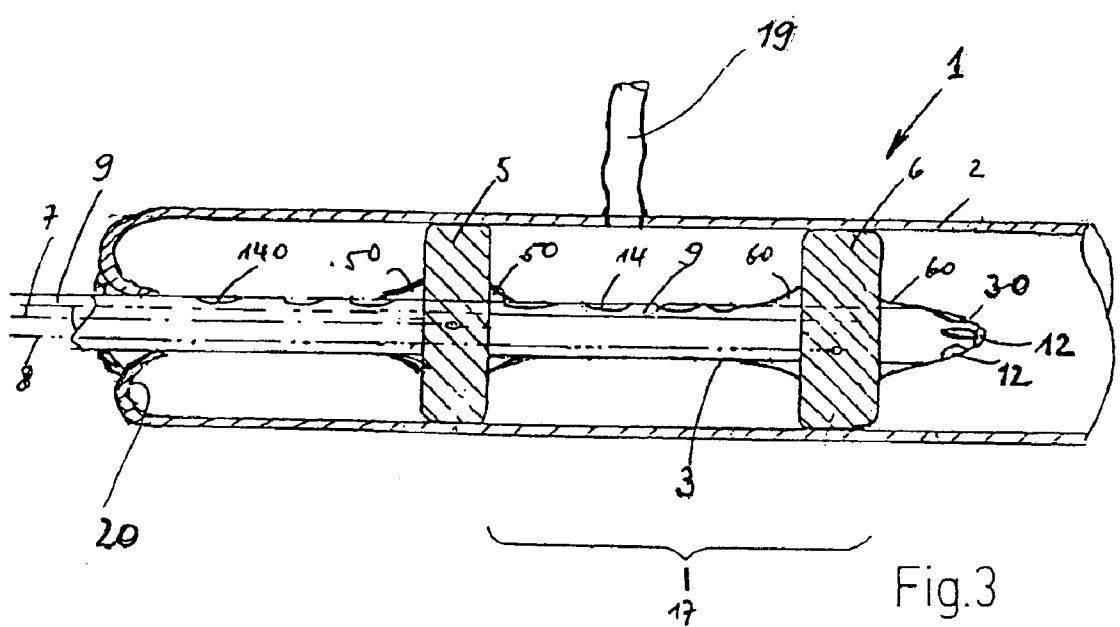
FIG. 3 is the balloon occlusion cannula according to FIG. 1 in an axial cut, in a side view and in a very simplified illustration.

The aortic balloon occlusion cannula, which is generally marked by a 1, is to occlude the ascending aorta indicated at 2, during cardiac surgeries. It contains a cannula tube 3 that is made out of an elastic material. This material enables the introduction of the cannula tube 3, while adapting to the required curvatures, into the ascending aorta 2 through a corresponding incision at 4 (FIG. 3) in the lefthand cardiac ventricle. When inserting the cannula care must be taken to pass the valvola aortae 20 as carefully as possible. Therefore, in the beginning a guide wire is placed into the heart and subsequently the cannula is inserted by means of a guide rod that is located in the cannula tube 3 and provided with a tapered end. This guide rod defines a lumen for said guide wire and is removed from the cannula tube 3 when the cannula is correctly inserted.

Cannula tube 3 can also be pre-shaped according to the curvature of the ascending aorta. Two dilatable occlusion balloons 5 and 6 that are positioned in a distance from each other, are mounted on the cannula tube 3. The first balloon 5 is positioned at the proximal end of the cannula tube 3, facing the heart, while the other balloon 6 ought to be in a distance of approximately 20 to 30 mm from the balloon 5, closer to the distal end of the cannula tube 3, facing the body.

The areas of the outer surface of the cannula tube 3 close to the two occlusions balloons 5, 6 are tapered or frustro-conically shaped at 50 and 60, respectively, or the cannula tube 3 is provided with a frustro-conical headpiece, which means enhance a smooth passage of the valvola aortae 20 when the cannula tube 3 is inserted or removed. For a similar reason the end portions 30 of the cannula tube 3 can be tapered to a point.

Both occlusions balloons 5, 6 consist of an elastic dilatable plastic, e.g. polyethylene which provides sufficient stiffness and consistency of shape in order to guarantee a secure closing of the ascending aorta 2. The diameter of the two balloons 5, 6 is adapted to the inner diameter of the ascending aorta 2 and its size is about 35–45 mm. The axial width of each of the two occlusion balloons is about 1.5 to 2 cm or more. Both occlusion balloons 5, 6 can be positioned on the cannula tube 3 either fixed or in such a way that they are movable towards each other in order to enable an adaption to the anatomic situation in each individual case.

Furthermore the two occlusion balloons can have different axial widthwise dimensions, the occlusion balloon 6 located close to the end being wider than the proximal occlusion balloon 5.

The cannula 1 contains several separate lumina. They form independent conduits and can be separated from one another as for instance indicated schematically in FIG. 2.

A first lumen 7, indicated in FIG. 3 by a chain doted line, leads to the first occlusion balloon 5 and permits its dilatation by means of a suitable dilatation liquid (physiologic salt solution). A second lumen 8, shown in FIG. 3 by a double chain dotted line, leads to the second occlusion balloon 6 and enables its dilatation by means of the corresponding dilatation liquid.

Outside of cannula tube 3, suitable fittings for the supply of dilatation liquid, shut-off valves and controls are assigned to the conduits formed by the lumina 7, 8 in order to dilate the occlusion balloons 5, 6 during the occlusion of the ascending aorta 2, and to return them into the non-dilated state. These means and devices are not illustrated in detail. They are well-known.

A third lumen 9 defines a conduit that opens via openings 140 on the proximal side, facing the heart, of the occlusion balloon 5. Said conduit is provided with additional openings 14 in the section between the two occlusion balloons 5 and 6. With the cannula 1 inserted and with an operative valvola aortae 20, liquid can be sucked-off the portion of the aorta ascendens 2 which is proximal to the occlusion balloon 5 through said openings 14. Furthermore, said conduit permits to suck liquid off the area between the two occlusion balloons 5 and 6 if the occlusion balloon 5 is not dilated or in case of a potential leakage of the occlusion balloon 5. The conduit defined by lumen 9 contains a shut-off organ 90 that permits the control of the supply of the heart protecting solution as required. The internal diameter of the lumen 9 is approximately 3 mm (to give an approximate size). The liquid rate for a retrograde myocardial perfusion is in the order of 500 ml per minute, at a maximum. Additional openings may be added to the third lumen which open to the left ventricle for venting. Alternatively, a separate lumen (not shown) may be included in the cannula that opens to the left ventricle for venting, if necessary.

A wider and larger lumen 11 is enclosed by the cannula tube 3. It is connected to the lumen of the distal part, i.e. the side facing the body, of the aorta ascendens when the cannula is inserted in the aorta 2 over one or more opening (s) 12 in the wall of the cannula 1. Lumen 11 forms a blood conduit that is, as indicated schematically in FIG. 1, connected to a heart-lung machine 13 which maintains the circulation extracorporally. The diameter of each of the openings 12 is 10 mm or more.

When the new cannula is used—this cannula can also be named as an aortic endoclamping cannula with double balloon technique and integrated cardioplegic cannula—at first the distal occlusion balloon 6 is dilated after the insertion of the cannula 1 in the aorta ascendens 2 through the incision 4 and the lefthand ventricle.

With the cannula 1 inserted and with the valvola aortae 20 being in an operative state a cardioplegic solution can be supplied to the heart through a coronary sinus 21 and a conduit 22 that is in the form of a coronary sinus catheter. Said cardioplegic solution is suctioned off through the conduit defining the lumen 9 while the body circulation is supplied with blood from the heart-lung machine 13 over the lumen 11 and the opening(s) 12. At this time the anastomoses located close to the heart are sutured.

Subsequently the second occlusion balloon 5 is dilated, so that the aorta ascendens 2 is additionally occluded at this place. The section 17 of the aorta ascendens 2 delimited between the two occlusion balloons 5 and 6 is opened and provided with "punched out" anastomotic holes, where upon the anastomoses are sutured. One of them is shown in FIG. 3 at 19. During these proceedings blood is supplied to the heart through the coronary sinus catheter 22. The blood is sucked-off through the conduit defining the lumen 9.

Upon the termination of these measures, the two occlusion balloons 5 and 6 are deflated, and the organism is trained to function without the heart-lung machine. The cannula 1 is taken out of the aorta ascendens 2 through the lefthand ventricle. The cannula tube 3 shows a generally straight or, according to the aorta curved section in the section 17 between the two occlusion balloons 5 and 6. As shown, the adjacent area 18 can lead approximately at right angles from the area 17.

What is claimed is:

1. A method of attaching a vein bypass to an ascending aorta of a heart of a body, comprising:

providing a cannula having two balloons and several lumina that are separated from one another, wherein the two balloons include a first dilatable occlusion balloon to be located proximal to the heart and a second dilatable occlusion balloon to be located distally to the heart, and wherein the plurality of separate lumens include a first lumen connected to the first balloon to enable dilation of the first balloon, a second lumen connected to the second balloon to enable dilation of the second balloon independent of the first balloon, and a third lumen that opens to the ascending aorta through an opening on a distal side of the second balloon;

connecting the third lumen to an extracorporal blood supply device;

inserting the cannula through left ventricle of the heart and upwardly through a valvola aortae of the heart;

positioning the two balloons in the ascending aorta such that the two balloons are positioned at a distance from each other along the ascending aorta;

dilating the two balloons;

attaching a vein bypass at the ascending aorta between the two balloons; and deflating the two balloons and removing the cannula from the body.

2. The method of claim 1 further comprising supplying cardioplegic solution to the heart.

3. The method of claim 2, wherein the cardioplegic solution is supplied through a coronary sinus.

4. The method of claim 2 wherein the cardioplegic solution is supplied by an additional separate lumen in the cannula.

5. The method of claim 1 wherein the several lumina include a separate lumen in addition to the first, second and third lumens, forming a return conduit for liquid and opening on the proximal side of the first balloon.

6. The method of claim 5, further comprising applying a vacuum in the separate lumen to suction off liquid in a portion of the ascending aorta which is on the proximal side of the first balloon.

7. The method of claim 5, wherein the separate lumen has a least one opening that opens between the first and second balloons.

8. The method of claim 7, further comprising applying a vacuum in the separate lumen to suction off liquid in a portion of the ascending aorta which is on the proximal side of the first balloon and to suction off liquid between the balloons.

9. The method of claim 1 further comprising forming an incision in the left ventricle of the heart and inserting the cannula through the incision in the left ventricle of the heart.

10. The method of claim 1 wherein the two balloons are dilated while positioned in the ascending aorta.

11. A method of attaching a vein bypass to an ascending aorta of a heart of a body, comprising:

providing a cannula having two balloons and several lumina that are separated from one another, wherein the two balloons include a first dilatable occlusion balloon to be located proximal to the heart and a second dilatable occlusion balloon to be located distally to the heart, and wherein the plurality of separate lumens include a first lumen connected to the first balloon to enable dilation of the first balloon, a second lumen connected to the second balloon to enable dilation of the second balloon independent of the first balloon, and a third lumen that opens to the ascending aorta through an opening on a distal side of the second balloon;

connecting the third lumen to an extracorporal blood supply device;

forming an incision in the left ventricle of the heart;

inserting the cannula through the incision in the left ventricle of the heart and upwardly through a valvola aortae of the heart;

positioning the two balloons in the ascending aorta such that the two balloons are positioned at a distance from each other along the ascending aorta;

dilating the two balloons while the two balloons are positioned in the ascending aorta;

attaching a vein bypass at the ascending aorta between the two balloons; and deflating the two balloons and removing the cannula from the body.

* * * * *